(12) United States Patent
Pak et al.

(10) Patent No.: US 8,349,765 B2
(45) Date of Patent: Jan. 8, 2013

(54) MULLITE-CONTAINING CARRIER FOR ETHYLENE OXIDE CATALYSTS

(75) Inventors: Serguei Pak, Teaneck, NJ (US);
Andrzej Rokicki, Mountain Lakes, NJ (US); Shuji Kawabata, Aichi (JP)

(73) Assignee: Scientific Design Company, Inc., Little Ferry, NJ (US)

( * ) Notice: Subject to any disclaimer, the term of this patent is extended or adjusted under 35 U.S.C. 154(b) by 2 days.

(21) Appl. No.: 12/360,457

(22) Filed: Jan. 27, 2009

(65) Prior Publication Data
US 2010/0016617 A1 Jan. 21, 2010

Related U.S. Application Data

(60) Provisional application No. 61/082,016, filed on Jul. 18, 2008.

(51) Int. Cl.
*B01J 21/04* (2006.01)
*C07D 301/03* (2006.01)

(52) U.S. Cl. ......................... 502/439; 549/523

(58) Field of Classification Search ............... 423/327.2; 549/523, 536, 537; 502/439
See application file for complete search history.

(56) References Cited

U.S. PATENT DOCUMENTS

| | | |
|---|---|---|
| 3,563,914 A | 2/1971 | Wattimena |
| 3,702,259 A | 11/1972 | Nielsen |
| 4,061,659 A | 12/1977 | Nielsen et al. |
| 4,087,385 A | 5/1978 | Wernli |
| 4,226,782 A | 10/1980 | Hayden et al. |
| 4,242,235 A | 12/1980 | Cognion et al. |
| 4,350,616 A | 9/1982 | Boussert |
| 4,740,493 A | 4/1988 | Boehning et al. |
| 4,761,394 A | 8/1988 | Lauritzen |
| 4,766,105 A | 8/1988 | Lauritzen |
| 4,908,343 A | 3/1990 | Bhasin |
| 5,011,807 A | 4/1991 | Hayden et al. |
| 5,055,442 A | 10/1991 | Osaka et al. |
| 5,057,481 A | 10/1991 | Bhasin |
| 5,099,041 A | 3/1992 | Hayden et al. |
| 5,100,859 A | 3/1992 | Gerdes et al. |
| 5,102,848 A | 4/1992 | Soo et al. |
| 5,112,795 A | 5/1992 | Minahan et al. |
| 5,145,824 A | 9/1992 | Buffum et al. |

(Continued)

FOREIGN PATENT DOCUMENTS
EP 2 017 004 1/2009

OTHER PUBLICATIONS

Lin et al, the Significance of the Mullite Phase in a Silver Catalyst for the Oxidation of Ethylene into Ethylene Oxide, 1983, Studies in Surface Science and Catalysis, vol. 16, p. 563-569.*

(Continued)

*Primary Examiner* — Taylor Victor Oh
(74) *Attorney, Agent, or Firm* — Scully, Scott, Murphy & Presser, P.C.

(57) ABSTRACT

The present invention relates to an improved carrier for an ethylene epoxidation catalyst, the carrier comprising alumina in combination with a stability-enhancing amount of mullite. The invention is also directed to an improved catalyst containing the improved carrier, as well as an improved process for the epoxidation of ethylene using the catalyst of the invention.

17 Claims, 1 Drawing Sheet

U.S. PATENT DOCUMENTS

| | | | |
|---|---|---|---|
| 5,187,140 | A | 2/1993 | Thorsteinson et al. |
| 5,266,548 | A | 11/1993 | Koradia et al. |
| 5,380,697 | A | 1/1995 | Matusz et al. |
| 5,387,751 | A | 2/1995 | Hayden et al. |
| 5,395,812 | A | 3/1995 | Nagase et al. |
| 5,407,888 | A | 4/1995 | Herzog et al. |
| 5,597,773 | A | 1/1997 | Evans et al. |
| 5,831,037 | A | 11/1998 | Ohsuga et al. |
| 6,103,916 | A | 8/2000 | Takada et al. |
| 6,281,370 | B1 | 8/2001 | Shima et al. |
| 6,571,214 | B2 | 5/2003 | Newman et al. |
| 6,717,001 | B2 | 4/2004 | Evans et al. |
| 6,815,395 | B2 | 11/2004 | Shima et al. |
| 6,831,037 | B2 | 12/2004 | Symanski et al. |
| 7,235,677 | B2 | 6/2007 | Chipman et al. |
| 7,388,119 | B2 | 6/2008 | Böttcher et al. |
| 2004/0110973 | A1 | 6/2004 | Matusz |
| 2005/0096219 | A1 | 5/2005 | Symanski et al. |
| 2006/0252643 | A1 | 11/2006 | Pak |
| 2009/0198076 | A1 * | 8/2009 | Guckel .................. 549/536 |

OTHER PUBLICATIONS

International Search Report dated Feb. 24, 2010 received from the Korean Intellectual Property Office.

\* cited by examiner

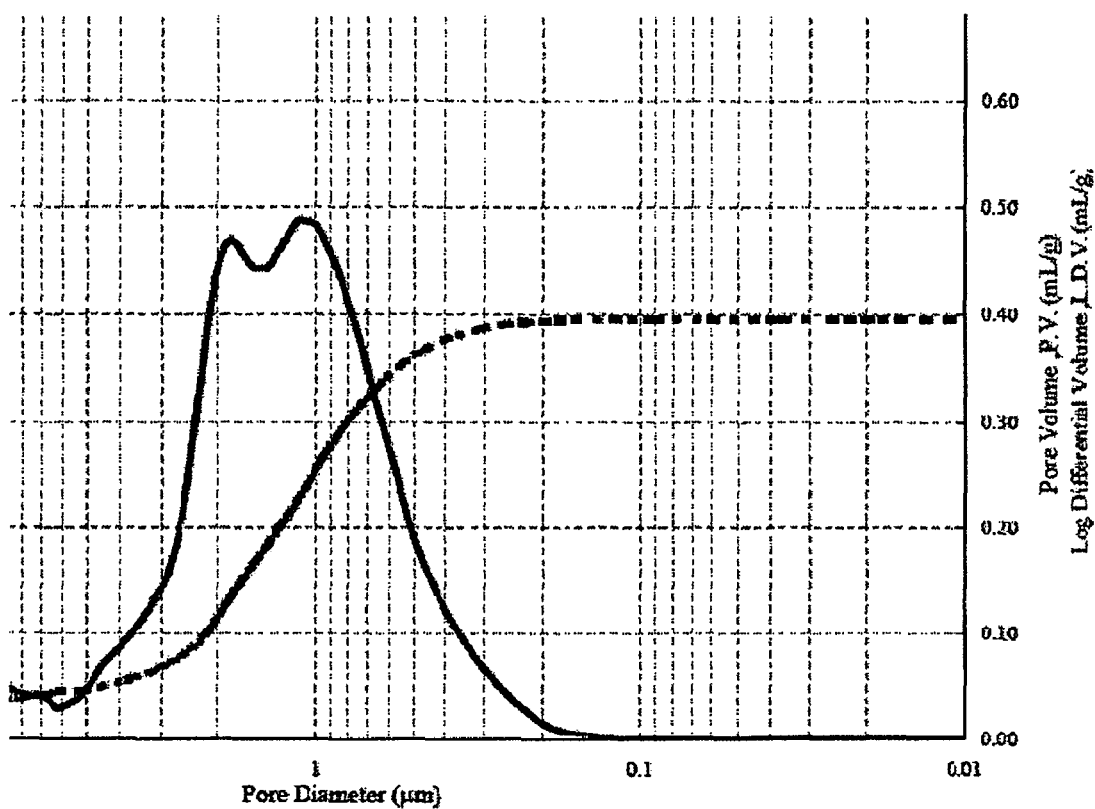

US 8,349,765 B2

MULLITE-CONTAINING CARRIER FOR ETHYLENE OXIDE CATALYSTS

RELATED APPLICATIONS

The present application is a non-provisional application of U.S. Provisional Application Ser. No. 61/082,016, filed Jul. 18, 2008, the entire contents of which are incorporated herein by reference. The present application asserts priority to the Jul. 18, 2008 filing date of the foregoing provisional application.

FIELD OF THE INVENTION

The present invention relates to silver-based ethylene oxide catalysts, and more particularly, to carriers for such catalysts.

BACKGROUND OF THE INVENTION

As known in the art, high selectivity catalysts (HSCs) for the epoxidation of ethylene refer to those catalysts that possess selectivity values higher than high activity catalysts (HACs) used for the same purpose. Both types of catalysts include silver as the active catalytic component on a refractory support (i.e., carrier). Typically, one or more promoters are included in the catalyst to improve or adjust properties of the catalyst, such as selectivity.

Generally, HSCs achieve the higher selectivity (typically, in excess of 87 mole % or above) by incorporation of rhenium as a promoter. Typically, one or more additional promoters selected from alkali metals (e.g., cesium), alkaline earth metals, transition metals (e.g., tungsten compounds), and main group metals (e.g., sulfur and/or halide compounds) are also included.

There are also ethylene epoxidation catalysts that may not possess the selectivity values typically associated with HSCs, though the selectivity values are improved over HACs. These types of catalysts can also be considered within the class of HSCs, or alternatively, they can be considered to belong to a separate class, e.g., "medium selectivity catalysts" or "MSCs." These types of catalysts typically exhibit selectivities of at least 83 mole % and up to 87 mole %.

In contrast to HSCs and MSCs, the HACs are ethylene epoxidation catalysts that generally do not include rhenium, and for this reason, do not provide the selectivity values of HSCs or MSCs. Typically, HACs include cesium (Cs) as the only promoter.

It is well known that with use of a catalyst, the catalyst will age (i.e., degrade) to a point until use of the catalyst is no longer practical. For obvious reasons, there is a continuous effort to extend the useful lifetime (i.e., "longevity" or "usable life") of catalysts. The useful lifetime of the catalyst is directly dependent on the stability of the catalyst. As used herein, the "useful lifetime" is the time period for which a catalyst can be used until one or more functional parameters, such as selectivity or activity, degrade to such a level that use of the catalyst becomes impractical.

It is known in the art that, while the selectivity of HSCs is generally acceptable to the industry, their useful lifetime can use improvement For example, while HACs typically last between 24 and 36 months, HSCs tend to be operated for less than 24 months, often less than 12 months, typically due to an unacceptable loss of selectivity.

Stability of the catalyst has largely been attributed to various characteristics of the carrier. Some characteristics of the carrier that have undergone much research include surface area, porosity, and pore volume distribution, among others.

The most widely used formulation for the carriers of ethylene epoxidation catalysts are those based on alumina, typically α-alumina. Much research has been directed to investigating the effect of the alumina composition for improving stability and other properties of the catalyst. The preparation and modification of alumina carriers for enhancing ethylene epoxidation catalyst performance are described, for example, in U.S. Pat. Nos. 4,226,782, 4,242,235, 5,266,548, 5,380,697, 5,597,773, 5,831,037 and 6,831,037 as well as in U.S. Patent Application Publication Nos. 2004/0110973 A1 and 2005/0096219 A1. In particular, U.S. Pat. No. 5,395,812 discloses coating the outer surface and surface of pores therein with an amorphous silica-alumina mixture in order to improve, inter alia, the lifetime of a silver-based ethylene epoxidation catalyst.

However, there remains a need in the art for further improvements in the stability of ethylene epoxidation catalysts. There is a particular need for improving the stability of such catalysts by modifying the carrier by means that are facile and financially feasible.

SUMMARY OF THE INVENTION

The present invention provides alumina carriers useful for preparing HSCs having an increased stability by incorporation therein of a stability-enhancing amount of mullite.

The invention is also directed to a stability-enhanced ethylene epoxidation catalyst comprising the stability-enhancing carrier described above, along with a catalytic amount of silver and a promoting amount of rhenium deposited on and/or in the carrier. The increased stability results in HSC (and MSC) catalysts with longer usable lifetimes, and particularly, catalysts that exhibit a significantly reduced degradation in selectivity as compared to such catalysts without the incorporation of mullite, over equivalent time periods of usage.

The invention is also directed to a method for the vapor phase conversion of ethylene to ethylene oxide (EO) in the presence of oxygen, the method comprising reacting a reaction mixture comprising ethylene and oxygen in the presence of the stability-enhanced ethylene epoxidation catalyst described above.

The invention provides a stability-enhanced ethylene epoxidation catalyst which is advantageously more resistant to degradation and retains a higher level of selectivity over time than similar catalysts that have not been stability-enhanced in accordance with the invention described herein. The invention is thus highly beneficial in that the longer catalyst life amounts to significant financial savings, greater efficiency of the process, and less process and catalyst waste.

BRIEF DESCRIPTION OF THE FIGURE

FIG. 1. Graph plotting pore diameter vs. pore volume (i.e., pore size distribution) of a carrier of the invention.

DETAILED DESCRIPTION OF THE INVENTION

In one aspect, the invention is directed to an improved alumina carrier for an ethylene epoxidation catalyst. The carrier is improved in that it imparts an enhanced stability to a silver-based catalyst derived therefrom.

The carrier (i.e., support) provides this enhanced stability by having incorporated therein a stability-enhancing amount of mullite within the alumina. As used herein, "mullite" (also known as "porcelainite") refers to an aluminum silicate mineral having an $Al_2O_3$ component combined as a solid solution with a $SiO_2$ phase, wherein the $Al_2O_3$ component is present in a concentration of at least about 40 mole percent and typically up to about 80 mole percent. More typically, mullite contains the $Al_2O_3$ component in a concentration of 60±5 mole percent, which can thus be approximately represented by the formula $3Al_2O_3 \cdot 2SiO_2$ (i.e., $Al_6Si_2O_{13}$).

Since natural sources of mullite are scarce, most commercial sources of mullite are synthetic. A variety of synthetic methods are known in the art. In one embodiment, the mullite used contains no other component other than the alumina and silica components described above, except for one or more components that may be present in trace amounts (e.g., less than 0.1 mole or weight percent). In another embodiment, the mullite used can include one or more additional components. For example, sodium oxide ($Na_2O$) can be included in a minor amount (typically no more than about 1.0 mole or weight percent). Other components, such as zirconia ($Zr_2O$) or silicon carbide (SiC) can be included to, for example, increase fracture toughness. Numerous other metal oxides can also be incorporated to alter the properties of the mullite.

A stability-enhancing amount of mullite is typically at least about 0.5% and up to about 20% of mullite by weight of the carrier. In one embodiment, the mullite is present in the carrier in a concentration of at least about 1 wt % and up to about 20 wt %, 15 wt %, 12 wt %, 10 wt %, 8 wt %, 6 wt %, 5 wt %, 4 wt %, 3 wt %, or 2 wt % of the carrier. In another embodiment, the mullite is present in the carrier in a concentration of at least about 3 wt % and up to about 20 wt %, 15 wt %, 12 wt %, 10 wt %, 8 wt %, 6 wt %, 5 wt %, or 4 wt % of the carrier. In yet another embodiment, the mullite is present in the carrier in a concentration of at least about 5 wt % and up to about 20 wt %, 15 wt %, 12 wt %, 10 wt %, 8 wt %, 7 wt %, or 6 wt % of the carrier. In still another embodiment, the mullite is present in the carrier in a concentration of at least about 7 wt % and up to about 20 wt %, 15 wt %, 12 wt %, 10 wt %, 9 wt %, or 8 wt %. In still other embodiments, the mullite can be present in the carrier within a concentration range of about 0.5-15 wt %, 0.5-12 wt %, 0.5-10 wt %, 0.5-8 wt %, 0.5-6 wt %, 0.5-5 wt %, 0.5-3 wt %, 0.5-2 wt %, 10-20 wt %, or 10-15 wt %.

In one embodiment, the outer surface of the alumina carrier is coated with mullite. The outer surface may be coated in conjunction with subsurface or interior portions of the carrier also containing mullite, or alternatively, in the absence of either subsurface or interior portions containing mullite.

In another embodiment, the outer surface of the alumina carrier is not coated with mullite while either a subsurface or interior region of the carrier contains mullite.

The carriers of the invention are composed of mullite and any of the refractory alumina compositions known in the art for use in ethylene oxidation catalysts. However, the preferred carriers are based on alpha-alumina and mullite. Typically, the catalyst is composed of alpha-alumina and mullite particles that are bonded together by a bonding agent. The alpha-alumina used in the inventive carrier preferably has a very high purity, i.e., about 95% or more, and more preferably, 98 wt. % or more alpha-alumina. Remaining components may be other phases of alumina, silica, alkali metal oxides (e.g., sodium oxide) and trace amounts of other metal-containing and/or non-metal-containing additives or impurities. Suitable alumina compositions are manufactured and/or commercially available from, for example, Noritake of Nagoya, Japan, and the NorPro Company of Akron, Ohio.

In general, a suitable catalyst carrier of the present invention can be prepared by combining the alumina, mullite, a solvent such as water, a temporary binder or burnout material, a permanent binder, and/or a porosity controlling agent, and then firing (i.e., calcining) the mixture by methods well known in the art.

Temporary binders, or burnout materials, include cellulose, substituted celluloses, e.g., methylcellulose, ethylcellulose, and carboxyethylcellulose, stearates (such as organic stearate esters, e.g., methyl or ethyl stearate), waxes, granulated polyolefins (e.g., polyethylene and polypropylene), walnut shell flour, and the like, which are decomposable at the temperatures employed. The binders are responsible for imparting porosity to the carrier material. Burnout material is used primarily to ensure the preservation of a porous structure during the green (i.e., unfired phase) in which the mixture may be shaped into particles by molding or extrusion processes. Burnout materials are essentially completely removed during the firing to produce the finished carrier.

The carriers of the invention are preferably prepared with the inclusion of a binder material in sufficient amount to substantially prevent the formation of crystalline silica compounds. Permanent binders include, for example, inorganic clay-type materials, such as silica and an alkali metal compound. A convenient binder material which may be incorporated with the alumina particles is a mixture of boehmite, an ammonia-stabilized silica sol, and a soluble sodium salt.

The formed paste is extruded or molded into the desired shape and fired at a temperature typically from about 1200° C. to about 1600° C. to form the carrier. Where the particles are formed by extrusion, it may be desirable to include conventional extrusion aids. Generally, the performance of the carrier is enhanced if it is treated by soaking the carrier in a solution of an alkali hydroxide such as sodium hydroxide, potassium hydroxide, or an acid such as $HNO_3$ as described in U.S. Patent Application Publication No. 2006/0252643 A1. After treatment, the carrier is preferably washed, such as with water, to remove unreacted dissolved material and treating solution, and then optionally dried.

The carrier of the invention is preferably porous and typically has a B.E.T. surface area of at most 20 $m^2/g$. The B.E.T. surface area is more typically in the range of about 0.1 to 10 $m^2/g$, and more typically from 1 to 5 $m^2/g$. In other embodiments, the carriers of the invention are characterized by having a B.E.T. surface area from about 0.3 $m^2/g$ to about 3 $m^2/g$, preferably from about 0.6 $m^2/g$ to about 2.5 $m^2/g$, and more preferably from about 0.7 $m^2/g$ to about 2.0 $m^2/g$. The B.E.T. surface area described herein can be measured by any suitable method, but is more preferably obtained by the method described in Brunauer, S., et al., *J. Am. Chem. Soc.*, 60, 309-16 (1938). The final support typically possesses a water absorption value ranging from about 0.2 cc/g to about 0.8 cc/g, and more typically from about 0.25 cc/g to about 0.6 cc/g.

The carrier can have any suitable distribution of pore diameters. As used herein, the "pore diameter" is used interchangeably with "pore size". Typically, the pore diameters are at least about 0.01 microns (0.01 μm), and more typically, at least about 0.1 μm. In different embodiments, the pore diameters can be at least about 0.2 μm, or 0.3 μm, or 0.4 μm, or 0.5 μm, or 0.6 μm, or 0.7 μm, or 0.8 μm, or 0.9 μm, or 1.0 μm, or 1.5 μm, or 2.0 μm. Typically, the pore diameters are no more than about 50 μm, 40 μm, 30 μm, 20 μm, or 10 μm. In particular embodiments, the pore diameters are no more than about 9 μm, or 8 μm, or 7 μm, or 6 μm, or 5 μm, or 4 pm, or 3 μm, or 2.5 μm. Any range derived from the foregoing minimum and maximum exemplary values is also suitable herein. In different embodiments, the suitable pore diameter range can be, for example, any one of 0.01-50 μm, 1-50 μm, 2-50 μm, 5-50 μm, 10-50 μm, 20-50 μm, 30-50 μm, 0.01-40 μm, 1-40 µm, 2-40 µm, 5-40 µm, 10-40 µm, 20-40 µm, 30-40 µm, 0.01-30 µm, 0.05-30 µm, 0.1-30 µm, 0.5-30 µm, 1-30 µm, 2-30 µm, 3-30 µm, 4-30 µm, 5-30 µm, 10-30 µm, 15-30 µm, 20-30 µm, 0.01-10 µm, 0.05-10 µm, 0.1-10 µm, 0.5-10 µm, 1-10 µm, 2-10 µm, 3-10 µm, 4-10 µm, 5-10 µm, 6-10 µm, 7-10 µm, 8-10 µm, 9-10 µm, 0.01-8 µm, 0.05-8 µm, 0.1-8 µm, 0.5-8 µm, 1-8 µm, 1.5-8 µm, 2-8 µm, 2.5-8 µm, 3-8 µm, 4-8 µm, 5-8 µm, 6-8 µm, 7-8 µm, 0.01-6 µm, 0.05-6 µm, 0.1-6 µm, 0.5-6 µm, 1-6 µm, 1.5-6 µm, 2-6 µm, 2.5-6 µm, 3-6 µm, 4-6 µm, 5-6 µm, 0.01-5 µm, 0.05-5 µm, 0.1-5 µm, 0.5-5 µm, 1-5 µm, 1.5-5 µm, 2-5 µm, 2.5-5 µm, 3-5 µm, 3.5-5 µm, 4-5 µm, 0.01-4 µm, 0.05-4 µm, 0.1-4 µm, 0.5-4 µm, 1-4 µm, 1.5-4 µm, 2-4 µm, 2.5-4 µm, 3-4 µM, 3.5-4 µm, 0.01-3 µm, 0.05-3 µm, 0.1-3 µm, 0.5-3 µm, 1-3 µm, 1.5-3 µm, 2-3 µm, 2.5-3 µm, 0.01-2 µm, 0.05-2 µm, 0.1-2 µm, 0.5-2 µm, 1-2 µm, and 1.5-2 µm, as long as the range of each mode of pores is different and each range possesses a different pore size of maximum concentration.

In a particular embodiment, the carrier possesses a multimodal pore size distribution (i.e., different pore size ranges, each range possessing a different pore size of maximum concentration). The multimodal pore size distribution is at least bimodal, and can thus be trimodal, tetramodal, or of a higher modality. The multimodal pore size distribution is characterized by the presence of at least two distributions (modes) of pore sizes, each pore size distribution being either overlapping or non-overlapping with another pore size distribution, and each pore size distribution having its own range of pore sizes (pore diameters) and peak concentration (typically expressed as peak pore volume). Each pore size distribution can be characterized by a single mean pore size (mean pore diameter) value. Accordingly, a mean pore size value given for a pore size distribution necessarily corresponds to a range of pore sizes that result in the indicated mean pore size value.

The first mode and second mode of pores possess different mean pore sizes (i.e., different mean pore diameters). Preferably, at least one of the modes of pores has a mean pore diameter within the range of about 0.01 µm to about 5 µm. More preferably, both a first and second mode of pores have a mean pore diameter within the range of about 0.01 µm to about 5 µm as long as the mean pore diameters are different. For example, at least one of the first and second mode of pores can have a mean pore size of about 0.01 µm, 0.02 µm, 0.03 µm, 0.04 µm, 0.05 µm, 0.06 µm, 0.07 µm, 0.08 µm, 0.09 µm, 0.1 µm, 0.2 µm, 0.3 µm, 0.4 µm, 0.5 µm, 0.6 µm, 0.7 µm, 0.8 µm, 0.9 µm, 1.0 µm, 1.1 µm, 1.2 µm, 1.3 µm, 1.4 µm, 1.5 µm, 1.6 µm, 1.7 µm, 1.8 µm, 1.9 µm, 2.0 µm, 2.1 µm, 2.2 µm, 2.3 µm, 2.4 µm, 2.5 µm, 2.6 µm, 2.7 µm, 2.8 µm, 2.9 µm, 3.0 µm, 3.1 µm, 3.2 µm, 3.3 µm, 3.4 µm, 3.5 µm, 3.6 µm, 3.7 µm, 3.8 µm, 3.9 µm, 4.0 µm, 4.1 µm, 4.2 µm, 4.3 µm, 4.4 µm, 4.5 µm, 4.6 µm, 4.7 µm, 4.8 µm, 4.9 µm, or 5.0 µm. Two or more modes of pores can also be independently selected from any of the above mean pore sizes as long as the mean pore sizes for each mode of pores are different. Any range derived from any two values recited above are also contemplated herein.

In another embodiment, at least one mode of pores is characterized by having a mean pore diameter above 5 µm up to about 30 µm. For example, in different embodiments, at least one mode of pores can have a mean pore diameter above 5 µm to about 25 µm, or above 5 µm to about 20 µm, or above 5 µm to about 15 µm, or above 5 µm to about 10 µm, or about 6 µm to about 30 µm, or about 7 µm to about 30 µm, or about 8 µm to about 30 µm, or about 10 µm to about 30 µm, or about 10 µm to about 25 µm, or about 10 µm to about 20 µm, or about 15 µm to about 30 µm. In one embodiment, one mode of pores has a mean pore diameter within the range of about 0.01 µm to about 5 µm (or any of the specific exemplary values given above within this range, or sub-ranges derived therefrom) while another mode of pores has a mean pore diameter above 5 µm up to about 30 µm, or any of the sub-ranges given therein. In another embodiment, at least two modes of pores have a mean pore diameter above 5 µm up to about 30 µm.

A preferred bimodal distribution for the carrier is depicted in FIG. 1. The solid line in FIG. 1 shows the distribution of pore diameters in the two modes by plotting pore diameter against pore volume distribution. One mode of pores is shown to have a range of pore sizes within about 0. 1 to 2.0 µm while another mode of pores is shown to have a range of pore sizes within about 0.5 or 1.0 to 5 µm. While the modes of pores are shown to significantly overlap in this instance, in other instances the modes of pores may overlap much less or not at all. The dashed line in FIG. 1 shows the pore diameter plotted against the logarithmic differential volume.

In a first embodiment, the first mode of pores comprises at most about 50% of the total pore volume and the second mode of pores comprises at least about 50% of the total pore volume. In a second embodiment, the first or second mode of pores comprises at most about 45% of the total pore volume and the other mode of pores comprises at least about 55% of the total pore volume. In a third embodiment, the first or second mode of pores comprises at most about 40% of the total pore volume and the other mode of pores comprises at least about 60% of the total pore volume. In a fourth embodiment, the first or second mode of pores comprises at most about 35% of the total pore volume and the other mode of pores comprises at least about 65% of the total pore volume. In a fifth embodiment, the first or second mode of pores comprises at most about 30% of the total pore volume and the other mode of pores comprises at least about 70% of the total pore volume. Numerous other embodiments reflective of different bimodal pore distributions are possible and within the scope of the present invention. Without wishing to be bound by any theory, it is believed that a catalyst with the described bimodal pore size distribution possesses a type of pore structure in which reaction chambers are separated by diffusion channels. The pore volume and pore size distribution described herein can be measured by any suitable method, but are more preferably obtained by the conventional mercury porosimeter method as described in, for example, Drake and Ritter, *Ind. Eng. Chem. Anal. Ed.,* 17, 787 (1945).

Preferably, the mean pore diameter of the first mode of pores and the mean pore diameter of the second mode of pores (i.e., the "differential in mean pore diameters") are different by at least about 0.1 µm. In different embodiments, the difference in mean pore sizes can be at least, for example, 0.2 µm, or 0.3 µm, or 0.4 µm, or 0.5 µm, or 0.6 µm, or 0.7 µm, or 0.8 µm, or 0.9 µm, or 1.0 µm, or 1.2 µm, or 1.4 µm, or 1.5 µm, 1.6 µm, or 1.8 µm, or 2.0 µm, or 2.5 µm, or 3 µm, or 4 µm, or 5 µm, or 6 µm, or 7 µm, or 8 µm, or 9 µm, or 10 µm, and up to about 15, 20 or 30 µm.

In a preferred carrier, at least 40% (and typically at least 60%, and more typically at least 80%) of the pore volume is due to pores with diameters between 1 and 5 micrometers. The median pore diameter of the carrier employed in the invention is typically between about 1 and 5 micrometers, more typically between about 1 and 4.5 micrometers, and even more typically between about 1 and 4 micrometers. The pore volume from pores with a diameter of 5 micrometers and above is typically less than about 0.20 ml/g, more typically less than about 0.10 ml/g, and even more typically less than about 0.05 ml/g. The pore volume from pores with a diameter of 1 micrometer and less is typically less than about 0.20 ml/g, more typically less than about 0.16 ml/g, and even more typically, less than about 0.12 ml/g. In some embodiments, the water pore volume can be from about 0.10 cc/g to about 0.80 cc/g, and more typically from about 0.20 cc/g to about 0.60 cc/g. The pore volume and pore size distribution described herein can be measured by any suitable method, but are more preferably obtained by the conventional mercury porosimeter method as described in, for example, Drake and Ritter, "Ind. Eng. Chem. Anal. Ed.," 17, 787 (1945).

The carrier of the invention can be of any suitable shape or morphology. For example, the carrier can be in the form of particles, chunks, pellets, rings, spheres, three-holes, wagon wheels, cross-partitioned hollow cylinders, and the like, of a size preferably suitable for employment in fixed bed reactors. Typically, carrier particles have equivalent diameters in the range of from about 3 mm to about 12 mm, and more typically in the range of from about 5 mm to about 10 mm, which are usually compatible with the internal diameter of the tubular reactors in which the catalyst is placed. As known in the art, the term "equivalent diameter" is used to express the size of an irregularly-shaped object by expressing the size of the object in terms of the diameter of a sphere having the same volume as the irregularly-shaped object.

In one embodiment, the carrier of the invention contains essentially only alumina and mullite components in the absence of other metals or chemical compounds, except that trace quantities of other metals or compounds may be present. A trace amount is an amount low enough that the trace species does not observably affect functioning or ability of the catalyst.

In another embodiment, the carrier of the invention contains one or more promoting species. As used herein, a "promoting amount" of a certain component of a catalyst refers to an amount of that component that works effectively to provide an improvement in one or more of the catalytic properties of the catalyst when compared to a catalyst not containing said component. Examples of catalytic properties include, inter alia, operability (resistance to runaway), selectivity, activity, conversion, stability and yield. It is understood by one skilled in the art that one or more of the individual catalytic properties may be enhanced by the "promoting amount" while other catalytic properties may or may not be enhanced or may even be diminished. It is further understood that different catalytic properties may be enhanced at different operating conditions. For example, a catalyst having enhanced selectivity at one set of operating conditions may be operated at a different set of conditions wherein the improvement is exhibited in the activity rather than in the selectivity.

For example, the mullite-containing carrier described above may include a promoting amount of an alkali metal or a mixture of two or more alkali metals. Suitable alkali metal promoters include, for example, lithium, sodium, potassium, rubidium, cesium or combinations thereof. Cesium is often preferred, with combinations of cesium with other alkali metals also being preferred. The amount of alkali metal will typically range from about 10 ppm to about 3000 ppm, more typically from about 15 ppm to about 2000 ppm, more typically from about 20 ppm to about 1500 ppm, and even more typically from about 50 ppm to about 1000 ppm by weight of the total catalyst, expressed in terms of the alkali metal.

The carrier of the invention may also include a promoting amount of a Group IIA alkaline earth metal or a mixture of two or more Group IIA alkaline earth metals. Suitable alkaline earth metal promoters include, for example, beryllium, magnesium, calcium, strontium, and barium or combinations thereof. The amounts of alkaline earth metal promoters are used in similar amounts as the alkali metal promoters described above.

The carrier of the invention may also include a promoting amount of a main group element or a mixture of two or more main group elements. Suitable main group elements include any of the elements in Groups IIIA (boron group) to VIIA (halogen group) of the Periodic Table of the Elements. For example, the catalyst can include a promoting amount of one or more sulfur compounds, one or more phosphorus compounds, one or more boron compounds, one or more halogen-containing compounds, or combinations thereof. The catalyst can also include a main group element, aside from the halogens, in its elemental form.

The carrier of the invention may also include a promoting amount of a transition metal or a mixture of two or more transition metals. Suitable transition metals can include, for example, the elements from Groups IIIB (scandium group), IVB (titanium group), VB (vanadium group), VIB (chromium group), VIB (manganese group), VIIIB (iron, cobalt, nickel groups), IB (copper group), and IIB (zinc group) of the Periodic Table of the Elements, as well as combinations thereof. More typically, the transition metal is an early transition metal, i.e., from Groups IIIB, IVB, VB or VIB, such as, for example, hafnium, yttrium, molybdenum, tungsten, rhenium, chromium, titanium, zirconium, vanadium, tantalum, niobium, or a combination thereof.

The carrier of the invention may also include a promoting amount of a rare earth metal or a mixture of two or more rare earth metals. The rare earth metals include any of the elements having an atomic number of 57-103. Some examples of these elements include lanthanum (La), cerium (Ce), and samarium (Sm).

The transition metal or rare earth metal promoters are typically present in an amount of from about 0.1 micromoles per gram to about 10 micromoles per gram, more typically from about 0.2 micromoles per gram to about 5 micromoles per gram, and even more typically from about 0.5 micromoles per gram to about 4 micromoles per gram of total catalyst, expressed in terms of the metal.

All of these promoters, aside from the alkali metals, can be in any suitable form, including, for example, as zerovalent metals or higher valent metal ions.

Of the promoters listed, rhenium (Re) is preferred as a particularly efficacious promoter for ethylene epoxidation high selectivity catalysts. The rhenium component in the catalyst can be in any suitable form, but is more typically one or more rhenium-containing compounds (e.g., a rhenium oxide) or complexes. The rhenium can be present in an amount of, for example, about 0.001 wt. % to about 1 wt. %. More typically, the rhenium is present in amounts of, for example, about 0.005 wt. % to about 0.5 wt. %, and even more typically, from about 0.01 wt. % to about 0.05 wt. % based on the weight of the total catalyst including the support, expressed as rhenium metal.

In another aspect, the invention is directed to an ethylene epoxidation catalyst produced from the carrier described above. In order to produce the catalyst, a carrier having the above characteristics is then provided with a catalytically effective amount of silver thereon and/or therein. The catalysts are prepared by impregnating the carriers with silver ions, compounds, complexes, and/or salts dissolved in a suitable solvent sufficient to cause deposition of silver precursor compound onto and/or into the carrier. The carrier can be impregnated and incorporated with rhenium and silver, along with any desired promoters, by any of the conventional methods known in the art, e.g., by excess solution impregnation, incipient wetness impregnation, spray coating, and the like. Typically, the carrier material is placed in contact with the silver-containing solution until a sufficient amount of the solution is absorbed by the carrier. Preferably, the quantity of the silver-containing solution used to impregnate the carrier is no more than is necessary to fill the pore volume of the carrier. Infusion of the silver-containing solution into the carrier can be aided by application of a vacuum. A single impregnation or a series of impregnations, with or without intermediate drying, may be used, depending in part on the concentration of the silver component in the solution. Impregnation procedures are described in, for example, U.S. Pat. Nos. 4,761,394, 4,766,105, 4,908,343, 5,057,481, 5,187,140, 5,102,848, 5,011,807, 5,099,041 and 5,407,888, all of which are incorporated herein by reference. Known procedures for pre-deposition, co-deposition, and post-deposition of the various promoters can also be employed.

Silver compounds useful for impregnation include, for example, silver oxalate, silver nitrate, silver oxide, silver carbonate, a silver carboxylate, silver citrate, silver phthalate, silver lactate, silver propionate, silver butyrate and higher fatty acid salts and combinations thereof. The silver solution used to impregnate the carrier can contain any suitable solvent. The solvent can be, for example, water-based, organic-based, or a combination thereof. The solvent can have any suitable degree of polarity, including highly polar, moderately polar or non-polar, or substantially or completely non-polar. The solvent typically has sufficient solvating power to solubilize the solution components. Some examples of water-based solvents include water and water-alcohol mixtures. Some examples of organic-based solvents include, but are not limited to, alcohols (e.g., alkanols), glycols (e.g., alkyl glycols), ketones, aldehydes, amines, tetrahydrofuran, nitrobenzene, nitrotoluene, glymes (e.g., glyme, diglyme and tetraglyme), and the like, and their combinations. Organic-based solvents that have 1 to about 8 carbon atoms per molecule are preferred.

A wide variety of complexing or solubilizing agents may be employed to solubilize silver to the desired concentration in the impregnating medium. Useful complexing or solubilizing agents include amines, ammonia, lactic acid and combinations thereof. For example, the amine can be an alkylene diamine having from 1 to 5 carbon atoms. In a preferred embodiment, the solution comprises an aqueous solution of silver oxalate and ethylene diamine. The complexing/solubilizing agent may be present in the impregnating solution in an amount from about 0.1 to about 5.0 moles of ethylene diamine per mole of silver, preferably from about 0.2 to about 4.0 moles, and more preferably from about 0.3 to about 3.0 moles of ethylene diamine for each mole of silver.

The concentration of silver salt in the solution is typically in the range from about 0.1% by weight to the maximum permitted by the solubility of the particular silver salt in the solubilizing agent employed. More typically, the concentration of silver salt is from about 0.5% to 45% by weight of silver, and even more typically, from about 5 to 35% by weight.

The ethylene oxide (EO) catalyst contains a catalytically effective amount of silver metal to catalyze the synthesis of ethylene oxide from ethylene and oxygen. The silver can be located on the surface and/or throughout the pores of the refractory support. A catalytically effective amount of silver can be, for example, up to about 45% by weight of silver, expressed as metal, based on the total weight of the catalyst including the support. Silver contents, expressed as metal, of from about 1% to about 40% based on the total weight of the catalyst are more typical. In other embodiments, the silver content can be from, for example, about 1 to 35%, 5 to 35%, 1 to 30%, 5 to 30%, 1 to 25%, 5 to 25%, 1 to 20%, 5 to 20%, 8 to 40%, 8 to 35%, 8 to 30%, 10 to 40%, 10 to 35%, 10 to 25%, 12 to 40%, 12 to 35%, 12 to 30%, or 12 to 25%.

Rhenium is also preferably incorporated into the silver-containing catalyst in order to provide a high selectivity catalyst. The rhenium is incorporated in the promoting amounts described above either prior to (i.e., by prior incorporation into the carrier), coincidentally with, or subsequent to the deposition of the silver Any one or more other promoting species can also be incorporated into the carrier either prior to, coincidentally with, or subsequent to the deposition of the silver. In one preferred embodiment, additional promoters include one or more species selected from Cs, Li, W, and S. In another preferred embodiment, additional promoters include one or more species selected from Cs, Li, and S.

After impregnation with silver and any promoters, the impregnated carrier is removed from the solution and calcined for a time sufficient to reduce the silver component to metallic silver and to remove volatile decomposition products from the silver-containing support. The calcination is typically accomplished by heating the impregnated carrier, preferably at a gradual rate, to a temperature in a range of about 200° C. to about 600° C., more typically from about 200° C. to about 500° C., more typically from about 250° C. to about 500° C., and more typically from about 200° C. or 300° C. to about 450° C., at a reaction pressure in a range from about 0.5 to about 35 bar. In general, the higher the temperature, the shorter the required calcination period. A wide range of heating periods have been described in the art for the thermal treatment of impregnated supports. See, for example, U.S. Pat. No. 3,563,914, which indicates heating for less than 300 seconds, and U.S. Pat. No. 3,702,259, which discloses heating from 2 to 8 hours at a temperature of from 100° C. to 375° C. to reduce the silver salt in the catalyst. A continuous or step-wise heating program may be used for this purpose.

During calcination, the impregnated support is typically exposed to a gas atmosphere comprising an inert gas, such as nitrogen. The inert gas may also include a reducing agent.

In another aspect, the invention is directed to a method for the vapor phase production of ethylene oxide by conversion of ethylene to ethylene oxide in the presence of oxygen by use of the catalyst described above. Generally, the ethylene oxide production process is conducted by continuously contacting an oxygen-containing gas with ethylene in the presence of the catalyst at a temperature in the range from about 180° C. to about 330° C., more typically from about 200° C. to about 325° C., and more typically from about 225° C. to about 270° C., at a pressure which may vary from about atmospheric pressure to about 30 atmospheres depending on the mass velocity and productivity desired. Pressures in the range of from about atmospheric to about 500 psi are generally employed. Higher pressures may, however, be employed within the scope of the invention. Residence times in large-scale reactors are generally on the order of about 0.1 to about 5 seconds. A typical process for the oxidation of ethylene to ethylene oxide comprises the vapor phase oxidation of ethylene with molecular oxygen in the presence of the inventive catalyst in a fixed bed, tubular reactor. Conventional commercial fixed bed ethylene oxide reactors are typically in the form of a plurality of parallel elongated tubes (in a suitable shell). In one embodiment, the tubes are approximately 0.7 to 2.7 inches O.D. and 0.5 to 2.5 inches I.D. and 15-45 feet long filled with catalyst.

The inventive catalysts have been shown to be particularly selective catalysts in the oxidation of ethylene with molecular oxygen to ethylene oxide. The conditions for carrying out such an oxidation reaction in the presence of the catalyst of the present invention broadly comprise those described in the prior art. This applies, for example, to suitable temperatures, pressures, residence times, diluent materials (e.g., nitrogen, carbon dioxide, steam, argon, methane or other saturated hydrocarbons), the presence or absence of moderating agents to control the catalytic action (e.g., 1,2-dichloroethane, vinyl chloride or ethyl chloride), the desirability of employing recycle operations or applying successive conversion in different reactors to increase the yields of ethylene oxide, and any other special conditions which may be selected in processes for preparing ethylene oxide. Molecular oxygen employed as a reactant may be obtained from conventional sources. The suitable oxygen charge may be relatively pure oxygen, or a concentrated oxygen stream comprising oxygen in a major amount with lesser amounts of one or more diluents such as nitrogen or argon, or air.

In the production of ethylene oxide, reactant feed mixtures typically contain from about 0.5 to about 45% ethylene and from about 3 to about 15% oxygen, with the balance comprising comparatively inert materials including such substances as nitrogen, carbon dioxide, methane, ethane, argon and the like. Only a portion of the ethylene is typically reacted per pass over the catalyst. After separation of the desired ethylene oxide product and removal of an appropriate purge stream and carbon dioxide to prevent uncontrolled build up of inert products and/or by-products, unreacted materials are typically returned to the oxidation reactor. For purposes of illustration only, the following are conditions that are often used in current commercial ethylene oxide reactor units: a gas hourly space velocity (GHSV) of 1500-10,000 $h^{-1}$, a reactor inlet pressure of 150-400 psig, a coolant temperature of 180-315° C., an oxygen conversion level of 10-60%, and an EO production (work rate) of 100-300 kg EO per cubic meters of catalyst per hour. Typically, the feed composition at the reactor inlet comprises 1-40% ethylene, 3-12% oxygen, 0.3-40% $CO_2$, 0-3% ethane, 0.3-20 ppmv total concentration of organic chloride moderator, and the balance of the feed comprised of argon, methane, nitrogen, or mixtures thereof.

In other embodiments, the process of ethylene oxide production includes the addition of oxidizing gases to the feed to increase the efficiency of the process. For example, U.S. Pat. No. 5,112,795 discloses the addition of 5 ppm of nitric oxide to a gas feed having the following general composition: 8 volume % oxygen, 30 volume % ethylene, about 5 ppmw ethyl chloride, and the balance nitrogen.

The resulting ethylene oxide is separated and recovered from the reaction products using methods known in the art. The ethylene oxide process may include a gas recycle process wherein a portion or substantially all of the reactor effluent is readmitted to the reactor inlet after substantially or partially removing the ethylene oxide product and any byproducts. In the recycle mode, carbon dioxide concentrations in the gas inlet to the reactor may be, for example, from about 0.3 to about 6 volume percent.

Examples have been set forth below for the purpose of farther illustrating the invention. The scope of this invention is not to be in any way limited by the examples set forth herein.

COMPARATIVE EXAMPLE 1

HAC Catalysts Prepared on Mullite-Free and Mullite-Containing Supports

An HAC catalyst was prepared on a mullite-free alpha-alumina support at a silver concentration, i.e., [Ag], of 11.6% and cesium concentration, i.e., [Cs], of 472 ppm.

A separate HAC catalyst was prepared on a mullite-containing (ca. 9% by weight mullite) alpha-alumina carrier with [Ag]=11.7% and [Cs]=440 ppm.

The two HAC catalysts were then subjected to an accelerated aging test at weight work rate (WWR)=737 g EO per 1 kg catalyst per 1 hour.

The performance results for the catalyst are shown below in Table 1. As shown in the table, the two HAC catalysts exhibited the same change in selectivity over 1000 hours (i.e., $\Delta S_{1000h}$=0) regardless of whether the carrier included or excluded mullite. Accordingly, it is evident that a conventional HAG catalyst does not require stability enhancement.

TABLE 1

Performance of HACs in an accelerated evaluation test

| Carrier | $S_{SOR}$[1] | $\Delta S_{1000\,h}$ |
|---|---|---|
| No mullite | 82.2 | 0 |
| 9% mullite | 82.3 | 0 |

[1]Start of Run (SOR) selectivity is measured after activation of catalyst to target work rate

EXAMPLE 2

HSC Catalysts Prepared on Mullite-Free and Mullite-Containing Supports

The HSC catalysts described below are based on alpha-alumina carriers containing the following promoters: Cs (as CsOH), Li (as $LiNO_3$), Re (as $HReO_4$), W (as ammonium metatungstate), and S (as ammonium sulfate). Promoter concentrations were optimized to provide maximum stability at high selectivity and were within the ranges found within examples 3-10 through 7-20 of U.S. Pat. No. 4,766,105.

An HSC catalyst was prepared on a mullite-free alpha-alumina carrier having the above promoter composition and with [Ag]=11.7%. This catalyst is herein referred to as catalyst HSC-1.

A separate HSC catalyst was prepared on a mullite-containing (ca. 9% by weight mullite) alpha-alumina carrier having the above promoter composition and with [Ag]=14.5%. This catalyst is herein referred to as catalyst HSC-2.

A separate HSC catalyst was prepared on a mullite-containing (ca. 9% by weight mullite) alpha-alumina carrier having the above promoter composition and with [Ag]=16.5%. This catalyst is herein referred to as catalyst HSC-3.

The three HSC catalysts were then subjected to an HSC accelerated aging test at weight work rate (WWR)=540 (g EO per 1 kg catalyst per 1 hour). The performance results for the HSC catalysts are shown below in Table 2. As shown in the table, the HSC catalyst not containing mullite (HSC-1) exhibits a change in selectivity over 1000 hours ($\Delta S_{1000h}$) of 4.6. In contrast, it has been surprisingly found that the two HSC catalysts containing mullite (i.e., HSC-2 and HSC-3) exhibit, respectively, a significantly reduced $\Delta S_{10000h}$ of <0.3 and 0.8, respectively. Therefore, it is evident from the data shown above that the mullite-containing HSC catalyst of the invention is significantly improved in stability, and hence, longevity, by an improved retention of selectivity as compared to HSC catalysts of the prior art over the same time period of operation.

TABLE 2

| Performance of HSCs in an accelerated evaluation test | | | |
|---|---|---|---|
| Carrier | $S_{MAX}$[2] | $S_{AV1500\,h}$[3] | $\Delta S_{1000\,h}$ |
| No mullite (HSC-1) | 89.5 | 86.9 | 4.6 |
| 9% mullite (HSC-2) | 88.5 | 88.2 | <0.3 |
| 9% mullite (HSC-3) | 89.8 | 89.2 | 0.8 |

[2] $S_{MAX}$ is maximum measured selectivity after reaching the target work rate.
[3] $S_{AV1500\,h}$ is calculated average selectivity in the 1500 hour test at target work rate.

The inventors have made the surprising and unexpected discovery that, whereas HAC catalysts do not exhibit a beneficial effect from incorporation of mullite, HSC catalysts show a pronounced improvement in retention of selectivity, and hence, usable lifetime of the catalyst when mullite is incorporated into their carriers at the same concentration.

While there have been shown and described what are presently believed to be the preferred embodiments of the present invention, those skilled in the art will realize that other and further embodiments can be made without departing from the spirit and scope of the invention described in this application, and this application includes all such modifications that are within the intended scope of the claims set forth herein.

What is claimed is:

1. A carrier for an ethylene epoxidation catalyst, the carrier comprising alumina in combination with a stability-enhancing amount of mullite, wherein the carrier possesses a multimodal pore size distribution.

2. The carrier according to claim 1, wherein the alumina is α-alumina.

3. The carrier according to claim 1, further comprising a promoting amount of rhenium.

4. The carrier according to claim 1, further comprising a promoting amount of an alkali or alkaline earth metal.

5. The carrier according to claim 1, further comprising a promoting amount of cesium.

6. The carrier according to claim 1, wherein the carrier possesses pores having diameters of at least about 0.01 μm and up to about 5 μm.

7. The carrier according to claim 1, wherein the carrier possesses a bimodal distribution of pore sizes comprising a first and a second distribution of pore sizes, wherein each distribution of pore sizes possesses a different mean pore size.

8. The carrier according to claim 7, wherein at least one distribution of pore sizes possesses a mean pore size within the range 0.01-5 μm.

9. The carrier according to claim 7, wherein the first and second distribution of pore sizes each possesses a mean pore size within the range 0.01-5 μm.

10. The carrier according to claim 1, wherein said stability-enhancing amount of mullite is about 7-15% mullite.

11. The carrier according to claim 1, wherein said stability-enhancing amount of mullite is about 7-10% mullite.

12. The carrier according to claim 1, wherein said stability-enhancing amount of mullite is about 7-20% mullite.

13. The carrier according to claim 1, wherein the stability-enhancing amount of mullite is about 0.5-20% mullite.

14. The carrier according to claim 1, wherein the stability-enhancing amount of mullite is about 1-15% mullite.

15. The carrier according to claim 1, wherein the stability-enhancing amount of mullite is about 1-12% mullite.

16. The carrier according to claim 1, wherein the stability-enhancing amount of mullite is about 3-15% mullite.

17. The carrier according to claim 1, wherein the stability-enhancing amount of mullite is about 3-12% mullite.

* * * * *